(12) United States Patent
Arcot-Krishnamurthy et al.

(10) Patent No.: US 8,958,873 B2
(45) Date of Patent: Feb. 17, 2015

(54) METHOD AND APPARATUS FOR SAFE AND EFFICIENT DELIVERY OF CARDIAC STRESS AUGMENTATION PACING

(75) Inventors: Shantha Arcot-Krishnamurthy, Vadnais Heights, MN (US); Allan C. Shuros, St. Paul, MN (US); Craig Stolen, New Brighton, MN (US); Robert Shipley, Austin, TX (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 810 days.

(21) Appl. No.: 12/770,351

(22) Filed: Apr. 29, 2010

(65) Prior Publication Data

US 2010/0305648 A1    Dec. 2, 2010

Related U.S. Application Data

(60) Provisional application No. 61/181,991, filed on May 28, 2009.

(51) Int. Cl.
*A61N 1/365* (2006.01)
*A61N 1/362* (2006.01)
*A61N 1/37* (2006.01)

(52) U.S. Cl.
CPC .............. *A61N 1/3627* (2013.01); *A61N 1/37* (2013.01)
USPC .................................. 607/21; 607/9; 607/17

(58) Field of Classification Search
USPC .......................................... 607/9, 17, 21, 22
See application file for complete search history.

(56) References Cited

U.S. PATENT DOCUMENTS

| | | | |
|---|---|---|---|
| 3,650,277 A | 3/1972 | Sjostrand et al. | |
| 4,587,975 A | 5/1986 | Salo et al. | |
| 4,722,342 A * | 2/1988 | Amundson | 607/20 |
| 4,730,619 A | 3/1988 | Koning et al. | |
| 4,791,931 A | 12/1988 | Slate | |
| 4,834,710 A | 5/1989 | Fleck | |
| 4,919,133 A | 4/1990 | Chiang | |
| 5,007,427 A | 4/1991 | Sukuki et al. | |
| 5,014,702 A * | 5/1991 | Alt | 607/19 |

(Continued)

FOREIGN PATENT DOCUMENTS

| | | |
|---|---|---|
| EP | 0547734 A2 | 6/1993 |
| EP | 0879618 A1 | 11/1998 |

(Continued)

OTHER PUBLICATIONS

"U.S. Appl. No. 11/682,448, Non-Final Office Action mailed Apr. 5, 2010", 17 pgs.

(Continued)

*Primary Examiner* — Alyssa M Alter
(74) *Attorney, Agent, or Firm* — Schwegman Lundberg & Woessner, P.A.

(57) ABSTRACT

A cardiac pacing system controls the progression of a cardiac disorder such as heart failure by delivering cardiac stress augmentation pacing to create or augment regional stress in the heart according to a delivery schedule programmed for a patient. Various events associated with the patient's conditions, activities, and other treatments may render the cardiac stress augmentation pacing risky or ineffective. The system detects such events before and during each cardiac stress augmentation pacing session and modifies the delivery schedule in response to the detection of each event to ensure patient safety and therapy efficiency.

21 Claims, 6 Drawing Sheets

(56) References Cited

U.S. PATENT DOCUMENTS

| | | |
|---|---|---|
| 5,024,222 A | 6/1991 | Thacker |
| 5,058,584 A | 10/1991 | Bourgeois |
| 5,072,458 A | 12/1991 | Suzuki |
| 5,111,818 A | 5/1992 | Suzuki et al. |
| 5,135,004 A | 8/1992 | Adams et al. |
| 5,184,615 A | 2/1993 | Nappholz et al. |
| 5,199,428 A | 4/1993 | Obel et al. |
| 5,282,840 A | 2/1994 | Hudrlik et al. |
| 5,313,953 A | 5/1994 | Yomtov et al. |
| 5,360,436 A | 11/1994 | Alt et al. |
| 5,376,106 A | 12/1994 | Stahmann et al. |
| 5,391,188 A | 2/1995 | Nelson et al. |
| 5,484,419 A | 1/1996 | Fleck |
| 5,531,768 A | 7/1996 | Alferness |
| 5,588,432 A | 12/1996 | Crowley |
| 5,634,899 A | 6/1997 | Shapland et al. |
| 5,649,968 A | 7/1997 | Alt et al. |
| 5,755,671 A | 5/1998 | Albrecht et al. |
| 5,824,021 A | 10/1998 | Rise |
| 5,919,209 A | 7/1999 | Schouten |
| 6,021,350 A | 2/2000 | Mathson |
| 6,058,331 A | 5/2000 | King |
| 6,104,956 A | 8/2000 | Naritoku et al. |
| 6,108,577 A | 8/2000 | Benser |
| 6,115,628 A | 9/2000 | Stadler et al. |
| 6,208,894 B1 * | 3/2001 | Schulman et al. .......... 607/2 |
| 6,233,486 B1 | 5/2001 | Ekwall et al. |
| 6,238,422 B1 | 5/2001 | Van Oort |
| 6,256,538 B1 | 7/2001 | Ekwall |
| 6,272,379 B1 | 8/2001 | Fischell et al. |
| 6,278,894 B1 | 8/2001 | Salo et al. |
| 6,285,907 B1 | 9/2001 | Kramer et al. |
| 6,314,323 B1 | 11/2001 | Ekwall et al. |
| 6,368,284 B1 | 4/2002 | Bardy |
| 6,408,208 B1 | 6/2002 | Sun |
| 6,411,845 B1 | 6/2002 | Mower |
| 6,445,953 B1 | 9/2002 | Bulkes et al. |
| 6,477,402 B1 | 11/2002 | Lynch et al. |
| 6,501,983 B1 | 12/2002 | Natarajan et al. |
| 6,569,145 B1 | 5/2003 | Shmulewitz et al. |
| 6,584,362 B1 | 6/2003 | Scheiner et al. |
| 6,604,000 B2 | 8/2003 | Lu |
| 6,610,713 B2 | 8/2003 | Tracey |
| 6,628,988 B2 | 9/2003 | Kramer et al. |
| 6,711,436 B1 | 3/2004 | Duhaylongsod |
| 6,735,479 B2 * | 5/2004 | Fabian et al. .......... 607/60 |
| 6,763,267 B2 | 7/2004 | Ding |
| 6,813,516 B2 | 11/2004 | Ujhelyi et al. |
| 6,827,690 B2 | 12/2004 | Bardy |
| 6,838,471 B2 | 1/2005 | Tracey |
| 6,842,642 B2 | 1/2005 | Vanhout |
| 6,845,267 B2 | 1/2005 | Harrison et al. |
| 6,865,420 B1 | 3/2005 | Kroll |
| 6,892,095 B2 | 5/2005 | Salo |
| 6,907,285 B2 | 6/2005 | Denker et al. |
| 6,913,577 B2 | 7/2005 | Bardy |
| 6,937,899 B2 | 8/2005 | Sheldon et al. |
| 6,950,701 B2 | 9/2005 | Begemann et al. |
| 6,965,797 B2 | 11/2005 | Pastore et al. |
| 6,973,349 B2 | 12/2005 | Salo |
| 7,010,345 B2 | 3/2006 | Hill et al. |
| 7,025,730 B2 | 4/2006 | Cho et al. |
| 7,039,462 B2 | 5/2006 | Pastore et al. |
| 7,043,305 B2 | 5/2006 | Kenknight et al. |
| 7,062,314 B2 | 6/2006 | Zhu et al. |
| 7,062,325 B1 | 6/2006 | Krig et al. |
| 7,069,070 B2 | 6/2006 | Carlson et al. |
| 7,072,711 B2 | 7/2006 | Girouard et al. |
| 7,092,755 B2 | 8/2006 | Florio |
| 7,158,832 B2 | 1/2007 | Kieval et al. |
| 7,171,258 B2 | 1/2007 | Goode |
| 7,215,992 B2 | 5/2007 | Stahmann et al. |
| 7,215,997 B2 | 5/2007 | Yu et al. |
| 7,277,761 B2 | 10/2007 | Shelchuk |
| 7,295,874 B2 | 11/2007 | Prinzen et al. |
| 7,299,087 B2 | 11/2007 | Bardy |
| 7,333,854 B1 | 2/2008 | Brewer et al. |
| 7,340,303 B2 | 3/2008 | Zhu |
| 7,364,547 B2 | 4/2008 | Stahmann et al. |
| 7,366,568 B2 | 4/2008 | Pastore et al. |
| 7,437,191 B2 | 10/2008 | Pastore et al. |
| 7,450,988 B2 | 11/2008 | Ross et al. |
| 7,460,906 B2 | 12/2008 | Libbus |
| 7,479,112 B2 | 1/2009 | Sweeney et al. |
| 7,486,991 B2 | 2/2009 | Libbus et al. |
| 7,668,594 B2 | 2/2010 | Brockway et al. |
| 7,711,420 B2 | 5/2010 | Baynham et al. |
| 2002/0026222 A1 | 2/2002 | Schauerte et al. |
| 2002/0042632 A1 | 4/2002 | Iaizzo et al. |
| 2002/0072776 A1 | 6/2002 | Osorio et al. |
| 2002/0072777 A1 | 6/2002 | Lu |
| 2002/0082660 A1 | 6/2002 | Stahmann et al. |
| 2002/0091415 A1 | 7/2002 | Lovett et al. |
| 2002/0123772 A1 | 9/2002 | Sun et al. |
| 2002/0128563 A1 | 9/2002 | Carlson et al. |
| 2003/0004549 A1 | 1/2003 | Hill et al. |
| 2003/0009189 A1 | 1/2003 | Gilson et al. |
| 2003/0045908 A1 | 3/2003 | Condie et al. |
| 2003/0055461 A1 | 3/2003 | Girouard et al. |
| 2003/0060854 A1 | 3/2003 | Zhu |
| 2003/0105493 A1 | 6/2003 | Salo |
| 2003/0120313 A1 | 6/2003 | Begemann et al. |
| 2003/0120315 A1 | 6/2003 | Spinelli et al. |
| 2003/0139778 A1 | 7/2003 | Fischell et al. |
| 2003/0158492 A1 | 8/2003 | Sheldon et al. |
| 2003/0158584 A1 | 8/2003 | Cates et al. |
| 2003/0199956 A1 | 10/2003 | Struble et al. |
| 2003/0204206 A1 | 10/2003 | Padua et al. |
| 2003/0204231 A1 | 10/2003 | Hine et al. |
| 2003/0229380 A1 | 12/2003 | Adams et al. |
| 2003/0233130 A1 | 12/2003 | Padmanabhan et al. |
| 2004/0015081 A1 | 1/2004 | Kramer et al. |
| 2004/0038947 A1 | 2/2004 | Wink et al. |
| 2004/0049235 A1 | 3/2004 | Deno et al. |
| 2004/0088015 A1 | 5/2004 | Casavant et al. |
| 2004/0088017 A1 | 5/2004 | Sharma et al. |
| 2004/0102815 A1 | 5/2004 | Balczewski et al. |
| 2004/0106960 A1 | 6/2004 | Siejko et al. |
| 2004/0106961 A1 | 6/2004 | Siejko et al. |
| 2004/0133247 A1 | 7/2004 | Stahmann et al. |
| 2004/0230240 A1 | 11/2004 | Sun et al. |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0043675 A1 | 2/2005 | Pastore et al. |
| 2005/0065568 A1 | 3/2005 | Liu et al. |
| 2005/0075673 A1 | 4/2005 | Warkentin et al. |
| 2005/0090719 A1 | 4/2005 | Scheiner et al. |
| 2005/0096705 A1 | 5/2005 | Pastore et al. |
| 2005/0096706 A1 | 5/2005 | Salo |
| 2005/0131467 A1 | 6/2005 | Boveja |
| 2005/0137631 A1 | 6/2005 | Yu et al. |
| 2005/0143779 A1 | 6/2005 | Libbus |
| 2005/0143780 A1 | 6/2005 | Henry et al. |
| 2005/0149126 A1 | 7/2005 | Libbus |
| 2005/0149127 A1 | 7/2005 | Libbus |
| 2005/0149129 A1 | 7/2005 | Libbus et al. |
| 2005/0171589 A1 | 8/2005 | Lau et al. |
| 2005/0197674 A1 | 9/2005 | McCabe et al. |
| 2005/0261741 A1 | 11/2005 | Libbus et al. |
| 2005/0283195 A1 | 12/2005 | Pastore et al. |
| 2005/0288721 A1 | 12/2005 | Girouard et al. |
| 2006/0020294 A1 | 1/2006 | Brockway et al. |
| 2006/0030892 A1 | 2/2006 | Kadhiresan et al. |
| 2006/0116593 A1 | 6/2006 | Zhang et al. |
| 2006/0136049 A1 | 6/2006 | Rojo |
| 2006/0149326 A1 | 7/2006 | Prinzen et al. |
| 2006/0195038 A1 | 8/2006 | Carlson et al. |
| 2006/0206158 A1 | 9/2006 | Wu et al. |
| 2006/0241357 A1 | 10/2006 | Chirife |
| 2006/0241704 A1 | 10/2006 | Shuros et al. |
| 2006/0247686 A1 | 11/2006 | Girouard et al. |
| 2006/0247700 A1 | 11/2006 | Jackson |
| 2006/0247702 A1 | 11/2006 | Stegemann et al. |

(56) References Cited

U.S. PATENT DOCUMENTS

| | | |
|---|---|---|
| 2006/0253156 A1 | 11/2006 | Pastore et al. |
| 2006/0259087 A1 | 11/2006 | Baynham et al. |
| 2006/0259088 A1 | 11/2006 | Pastore et al. |
| 2006/0271119 A1 | 11/2006 | Ni et al. |
| 2006/0282000 A1 | 12/2006 | Zhang et al. |
| 2006/0287684 A1 | 12/2006 | Baynham et al. |
| 2007/0021789 A1 | 1/2007 | Pastore et al. |
| 2007/0021790 A1 | 1/2007 | Kieval et al. |
| 2007/0021798 A1 | 1/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0043393 A1 | 2/2007 | Brockway et al. |
| 2007/0049835 A1 | 3/2007 | Goode |
| 2007/0054871 A1 | 3/2007 | Pastore et al. |
| 2007/0060972 A1 | 3/2007 | Kieval et al. |
| 2007/0142864 A1 | 6/2007 | Libbus et al. |
| 2007/0142871 A1 | 6/2007 | Libbus et al. |
| 2007/0150005 A1 | 6/2007 | Sih et al. |
| 2007/0150015 A1 | 6/2007 | Zhang et al. |
| 2007/0162081 A1 | 7/2007 | Yu et al. |
| 2007/0167984 A1 | 7/2007 | Kieval et al. |
| 2007/0179392 A1 | 8/2007 | Zhang |
| 2007/0191892 A1 | 8/2007 | Mullen et al. |
| 2007/0233192 A1* | 10/2007 | Craig .............................. 607/2 |
| 2007/0239218 A1 | 10/2007 | Carlson et al. |
| 2007/0282380 A1 | 12/2007 | Brooke et al. |
| 2007/0299356 A1 | 12/2007 | Wariar et al. |
| 2008/0004669 A1 | 1/2008 | Sathaye et al. |
| 2008/0015659 A1 | 1/2008 | Zhang et al. |
| 2008/0021507 A1 | 1/2008 | Libbus et al. |
| 2008/0027495 A1 | 1/2008 | Prinzen et al. |
| 2008/0058661 A1 | 3/2008 | Bardy |
| 2008/0058881 A1 | 3/2008 | Wagner et al. |
| 2008/0071315 A1 | 3/2008 | Baynham et al. |
| 2008/0081354 A1 | 4/2008 | Qu et al. |
| 2008/0082135 A1 | 4/2008 | Arcot-Krishnamurthy et al. |
| 2008/0091138 A1 | 4/2008 | Pastore et al. |
| 2008/0132972 A1 | 6/2008 | Shuros et al. |
| 2008/0140141 A1 | 6/2008 | Ben-David et al. |
| 2008/0167694 A1 | 7/2008 | Bolea et al. |
| 2008/0177156 A1 | 7/2008 | Zhang et al. |
| 2008/0177191 A1 | 7/2008 | Patangay et al. |
| 2008/0177194 A1 | 7/2008 | Zhang et al. |
| 2008/0215105 A1 | 9/2008 | Pastore et al. |
| 2008/0221636 A1 | 9/2008 | Pastore et al. |
| 2008/0234774 A1 | 9/2008 | Baynham et al. |
| 2009/0025459 A1 | 1/2009 | Zhang et al. |
| 2009/0048641 A1 | 2/2009 | Libbus |
| 2009/0082781 A1 | 3/2009 | Tran et al. |
| 2009/0124916 A1 | 5/2009 | Sweeney et al. |
| 2009/0192560 A1 | 7/2009 | Arcot-Krishnamurthy et al. |
| 2009/0234401 A1 | 9/2009 | Zielinski et al. |
| 2009/0281591 A1 | 11/2009 | Shuros et al. |
| 2009/0318984 A1 | 12/2009 | Mokelke et al. |
| 2010/0016913 A1 | 1/2010 | Arcot-Krishnamurthy et al. |
| 2010/0016916 A1 | 1/2010 | Arcot-Krishnamurthy et al. |
| 2010/0130913 A1 | 5/2010 | Baynham et al. |
| 2011/0071584 A1 | 3/2011 | Mokelke et al. |

FOREIGN PATENT DOCUMENTS

| | | |
|---|---|---|
| EP | 2000078391 A1 | 12/2000 |
| EP | 1437159 A1 | 7/2004 |
| EP | 1690566 A1 | 8/2006 |
| WO | WO-9302745 A1 | 2/1993 |
| WO | WO-9518649 A1 | 7/1995 |
| WO | WO-0078391 A1 | 12/2000 |
| WO | WO-0115609 A1 | 3/2001 |
| WO | WO-0124876 A1 | 4/2001 |
| WO | WO-0128625 | 4/2001 |
| WO | WO-0176689 A2 | 10/2001 |
| WO | WO-03082080 A2 | 10/2003 |
| WO | WO-2004024229 A1 | 3/2004 |
| WO | WO-2004058326 A2 | 7/2004 |
| WO | WO-2005042091 A1 | 5/2005 |
| WO | WO-2006074189 A1 | 7/2006 |
| WO | WO-2006079010 A1 | 7/2006 |
| WO | WO-2006105474 A2 | 10/2006 |
| WO | WO-2006115693 A2 | 11/2006 |
| WO | WO-2006115693 A3 | 11/2006 |
| WO | WO-2006121842 A2 | 11/2006 |
| WO | WO-2006124636 A2 | 11/2006 |
| WO | WO-2006124729 A2 | 11/2006 |
| WO | WO-2007078410 A1 | 7/2007 |
| WO | WO-2007133962 A2 | 11/2007 |
| WO | WO-2008063396 A1 | 5/2008 |
| WO | WO-2008109040 A2 | 9/2008 |

OTHER PUBLICATIONS

"International Application Serial No. PCT/US2008/002799, International Search Report mailed Oct. 15, 2008", 6 pgs.

"International Application Serial No. PCT/US2008/002799, Invitation to Pay Fees and Partial International Search Report mailed Jul. 14, 2008", 7 pgs.

"International Application Serial No. PCT/US2008/002799, Written Opinion mailed Oct. 15, 2008", 11 pgs.

Airaksinen, K. E., et al., "Antiarrhythmic effect of repeated coronary occlusion during balloon angioplasty", *J Am Coll Cardiol.*, 29(5), (Apr. 1997), 1035-1038.

Amende, I., "Hemodynamics in ischemia: diastolic phase", *Z. kardiol.*, 73 Suppl 2, [Article in German With English Abstract], (1984), 127-33.

Andersen, H, et al., "Long-term follow-up of patients from a randomised trial of atrial versus ventricular pacing for sick-sinus syndrome", *Lancet*, 350(9086), (Oct. 25, 1997), 1210-6.

Baynham, Tamara C, et al., "Integrated Catheter and Pulse Generator Systems and Methods", U.S. Appl. No. 11/468,875, filed Aug. 31, 2006, 23 Pages.

Benchimol, A, et al., "Cardiac hemodynamics during stimulation of the right atrium, right ventricle, and left ventricle in normal and abnormal hearts", *Circulation*, 33(6), (Jun. 1966), 933-44.

Dzwonczyk, R., et al., "Myocardial electrical impedance responds to ischemia and reperfusion in humans", *IEEE Transactions on Biomedical Engineering*, 51(12), (Dec. 2004), 2206-2209.

Girouard, Steven D., "Pulmonary Vein Stent for Treating Atrial Fibrillation", U.S. Appl. No. 60/298,741, filed Jun. 15, 2001, 14 pgs.

Grassi, Guido, et al., "Baroreflex and non-baroreflex modulation of vagal cardiac control after myocardial infarction", *Am J Cardiol.*, 84(5), (Sep. 1, 1999), 525-9.

Henriques, Jose P., et al., "Outcome of primary angioplasty for acute myocardial infarction during routine duty hours versus during off-hours", *J Am Coll Cardiol*, 41(12), (Jun. 18, 2003), 2138-2142.

Ishihara, M., et al., "Implications of prodromal angina pectoris in anterior wall acute myocardial infarction: acute angiographic findings and long-term prognosis", *J Am Coll Cardiol.*, 30(4), (1997), 970-5.

Kin, Hajime, et al., "Postconditioning attenuates myocardial ischemia-reperfusion injury by inhibiting events in the early minutes of reperfusion", *Cardiovascular Research*, 62(1), (Apr. 1, 2004), 74-85.

Kis, A., "Repeated cardiac pacing extends the time during which canine hearts are protected against ischaemia-induced arrhythmias: role of nitric oxide.", *Journal of Molecular and Cellular Cardiology*, 31(6), (Jun. 1999), 1229-1241.

Kloner, R. A., et al., "Prospective temporal analysis of the onset of preinfarction angina versus outcome: an ancillary study in TIMI-9B", *Circulation*, 97(11), (1998), 1042-5.

Koning, M M, "Rapid ventricular pacing produces myocardial protection by nonischemic activation of KATP+ channels", *Circulation*, 93(1), (Jan. 1, 1996), 178-186.

Krayenbuhl, H. P., "Hemodynamics in ischemia. Systolic phase", *Z. Kardiol.*, 73 Suppl 2, [Article in German with English Abstract], (1984), 119-25.

Leclercq, C, et al., "Hemodynamic importance of preserving the normal sequence of ventricular activation in permanent cardiac pacing", *Am Heart J.*, 129(6), (Jun. 1995), 1133-41.

(56) References Cited

OTHER PUBLICATIONS

Loukogeorgakis, S. P., et al., "Remote ischemic preconditioning provides early and late protection against endothelial ischemia-reperfusion injury in humans: role of the autonomic nervous system.", *J Am Coll Cardiol.*, 46(3), (Aug. 2, 2005), 450-6.

Makhoul, John, "Linear Prediction: A Tutorial Review", *Proceedings of the IEEE*, 63, (Apr. 1975), 561-580.

Meier, B., et al., "Coronary Pacing During Percutaneous Transluminal Coronary Angioplasty", *Circulation*, 71(3), (Mar. 1985), 557-561.

Murry, C. E., et al., "Preconditioning with ischemia: a delay of lethal cell injury in ischemic myocardium", *Circulation*, 74(5), (1986), 1124-1136.

Ovize, M., et al., "Stretch preconditions canine myocardium.", *Am J Physiol.*, 266(1 Pt 2), (Jan. 1994), H137-46.

Panju, Akbar A, et al., "Is This Patient Having a Myocardial Infraction?", *JAMA*, 280(14), (Oct. 14, 1998), 1256-1263.

Patangay, Ahilash, et al., "Ischemia Detection Using Heart Sound Timing", U.S. Appl. No. 11/625,003, filed Jan. 19, 2007, 69 Pages.

Prinzen, Frits W, "Mapping of regional myocardial strain and work during ventricular pacing: experimental study using magnetic resonance imaging tagging", *Journal of the American College of Cardiology*, 33(6), (May 1999), 1735-1742.

Rosa, A., et al., "Ectopic Pacing at Physiological Rate Improves Postanoxic Recovery of the Developing Heart", *Am. J. Physiol.—Heart Circ. Physiol.*, 284, (2003), H2384-H2392.

Rosenqvist, M, et al., "The effect of ventricular activation sequence on cardiac performance during pacing", *Pacing and Electrophysiology*, 19(9), (1996), 1279-1286.

Salerno, D. M., "Seismocardiography for monitoring changes in left ventricular function during ischemia.", *Chest*, 100(4), (Oct. 1991), 991-3.

Solomon, S. D., et al., "Angina pectoris prior to myocardial infarction protects against subsequent left ventricular remodeling", *J Am Coll Cardiol.*, 43(9), (2004), 1511-4.

Tavel, Morton E, "The Appearance of Gallop Rhythm after Exercise Stress Testing", *Clin. Cardiol.*, vol. 19, (1996), 887-891.

Tsang, A., et al., "Postconditioning: a form of "modified reperfusion" protects the myocardium by activating the phosphatidylinositol 3-kinase-Akt pathway", *Circ Res.*, 95(3), Epub Jul. 8, 2004, (Aug. 6, 2004), 230-2.

Vanagt, W. Y. R., et al., "Ventricular Pacing for Improving Myocardial Tolerance to Ischemic", *Progress Report on Project Guidant-CARIM*, (Oct. 2003), 1-25.

Vegh, A, et al., "Transient ischaemia induced by rapid cardiac pacing results in myocardial preconditioning", *Cardiovascular Research*, 25(12), (Dec. 1991), 1051-3.

Wu, Zhong-Kai, et al., "Ischemic preconditioning suppresses ventricular tachyarrhythmias after myocardial revascularization", *Circulation*, 106(24), (Dec. 10, 2002), 3091-3096.

Yang, S. M., et al., "Multiple, brief coronary occlusions during early reperfusion protect rabbit hearts by targeting cell signaling pathways", *Journal of the American College of Cardiology*, 44(5), (Sep. 1, 2004), 1103-1110.

Zhao, Zhi-Qing, et al., "Inhibition of myocardial injury by ischemic postconditioning during reperfusion: comparison with ischemic preconditioning", *Am J Physiol Heart Circ Physiol*, 285(2), (Aug. 2003), H579-H588.

"U.S. Appl. No. 11/681,448, Response filed May 14, 2013 to Final Office Action mailed Jan. 16, 2013", 12 pgs.

"U.S. Appl. No. 11/682,448, Advisory Action mailed Mar. 25, 2013", 4 pgs.

"U.S. Appl. No. 11/682,448, Final Office Action mailed Jan. 16, 2013", 9 pgs.

"U.S. Appl. No. 11/682,448, Notice of Allowance mailed Aug. 20, 2013", 6 pgs.

"U.S. Appl. No. 11/682,448, Response filed Mar. 4, 2013 to Final Office Action mailed Jan. 16, 2013", 13 pgs.

"U.S. Appl. No. 12/877,622, Response filed Sep. 12, 2013 to Restriction Requirement mailed Aug. 21, 2013", 8 pgs.

"U.S. Appl. No. 12/877,622, Restriction Requirement mailed Aug. 21, 2013", 7 pgs.

"U.S. Appl. No. 12/877,622, Non Final Office Action mailed Jan. 7, 2014", 10 pgs.

"U.S. Appl. No. 12/877,622, Notice of Allowance mailed Apr. 15, 2014", 5 pgs.

"U.S. Appl. No. 12/877,622, Response filed Mar. 25, 2014 to Non Final Office Action mailed Jan. 7, 2014", 9 pgs.

\* cited by examiner

METHOD AND APPARATUS FOR SAFE AND EFFICIENT DELIVERY OF CARDIAC STRESS AUGMENTATION PACING

CROSS-REFERENCE TO RELATED APPLICATIONS

This application claims the benefit of U.S. Provisional Application No. 61/181,991, filed on May 28, 2009, under 35 U.S.C. § 119(e), which is hereby incorporated by reference in its entirety.

This application is related to co-pending, commonly assigned, U.S. patent application Ser. No. 11/682,448, entitled "METHOD AND APPARATUS FOR CLOSED-LOOP INTERMITTENT STRESS AUGMENTATION PACING," filed on Mar. 6, 2007, which is hereby incorporated by reference in its entirety.

TECHNICAL FIELD

This document relates generally to cardiac rhythm management (CRM) systems and particularly a system providing for intermittent cardiac stress augmentation pacing with delivery controlled for patient safety and therapy efficiency.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. The pumping functions are accomplished by contractions of the myocardium (heart muscles). In a normal heart, the sinoatrial node, the heart's natural pacemaker, generates electrical impulses, known as action potentials that propagate through an electrical conduction system to various regions of the heart to excite myocardial tissues in these regions. Coordinated delays in the propagations of the action potentials in a normal electrical conduction system cause the various regions of the heart to contract in synchrony such that the pumping functions are performed efficiently.

A blocked or otherwise damaged electrical conduction system causes irregular contractions of the myocardium, a condition generally known as arrhythmia. Arrhythmia reduces the heart's pumping efficiency and hence, diminishes the blood flow to the body. A deteriorated myocardium has decreased contractility, also resulting in diminished blood flow. A heart failure patient usually suffers from both a damaged electrical conduction system and a deteriorated myocardium. The diminished blood flow results in insufficient blood supply to various body organs, preventing these organs to function properly and causing various symptoms.

Without timely and effective treatment, a cardiac disorder may develop to an extent that significantly lowers a patient's quality of life and threatens the patient's life. For example, heart failure may progress rapidly, with continuously deteriorating cardiac conditions and hemodynamic performance that could lead to inability to carry out daily activities and death. For these and other reasons, there is a need for controlling the progression of cardiac disorders, such as heart failure.

SUMMARY

A cardiac pacing system controls the progression of a cardiac disorder such as heart failure by delivering cardiac stress augmentation pacing to create or augment regional stress in the heart according to a delivery schedule programmed for a patient. Various events associated with the patient's conditions, activities, and other treatments may render the cardiac stress augmentation pacing risky or ineffective. The system detects such events before and during each cardiac stress augmentation pacing session and modifies the delivery schedule in response to the detection of each event to ensure patient safety and therapy efficiency.

In one embodiment, a cardiac pacing system includes a pacing output circuit to deliver pacing pulses and a pacing control circuit to control the delivery of the pacing pulses. The pacing control circuit includes a memory circuit, an inhibitory signal input, and a stress augmentation pacing controller. A delivery schedule is stored on the memory circuit. The delivery schedule specifies timing of stress augmentation pacing sessions each including a session duration during which the pacing pulses are delivered using pacing parameters selected to augment cardiac stress to a level effective in slowing or stopping progression of a cardiac disorder. The inhibitory signal input receives an inhibitory signal. If the inhibitory signal is not present at a scheduled beginning of a stress augmentation pacing session, the stress augmentation pacing controller initiates that stress augmentation pacing session. If the inhibitory signal is present at the scheduled beginning of a stress augmentation pacing session, the stress augmentation pacing controller reschedules one or more stress augmentation pacing sessions.

In one embodiment, a method for operating a cardiac pacing system is provided. Before initiating a stress augmentation pacing session according to a delivery schedule, whether an inhibitory signal is present is determined. The stress augmentation pacing session includes a session duration during which pacing pulses are delivered from an implantable medical device using pacing parameters selected to augment cardiac stress to a level effective in slowing or stopping progression of a cardiac disorder. If the inhibitory signal is not present, the stress augmentation pacing session is initiated according to the delivery schedule. If the inhibitory signal is present, one or more stress augmentation pacing sessions are rescheduled.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses a pacing system including an implantable medical device that controls progression of a cardiac disorder in a patient by applying therapy sessions during which cardiac stress augmentation pacing is delivered. The cardiac stress augmentation pacing (also referred to as "stress augmentation pacing" herein) creates or augments regional stress in the patient's heart, such as by selecting pacing parameters to increase the degree of ventricular asynchrony. During each therapy session, the pacing pulses are delivered according to a stress augmentation pacing sequence that includes alternating pacing and non-pacing periods or alternating periods of different pacing modes. The therapy sessions are initiated according to a programmed delivery schedule. However, the patient's physiological and pathological conditions, daily activities, and other medical treatments may not be precisely anticipated or planned for when the delivery schedule is programmed. Such conditions, daily activities, and treatments may potentially affect the safety and efficacy of the stress augmentation pacing. Therefore, the present system detects inhibitory events that may render the stress augmentation pacing ineffective and terminating events that may render the stress augmentation pacing harmful to the patient. If an inhibitory event is occurring at the time a therapy session is scheduled to begin, the present system modifies the delivery schedule to ensure efficiency of therapy. In response to the detection of a terminating event during a therapy session, the present system terminates that therapy session to ensure safety of the patient.

Figure 1:
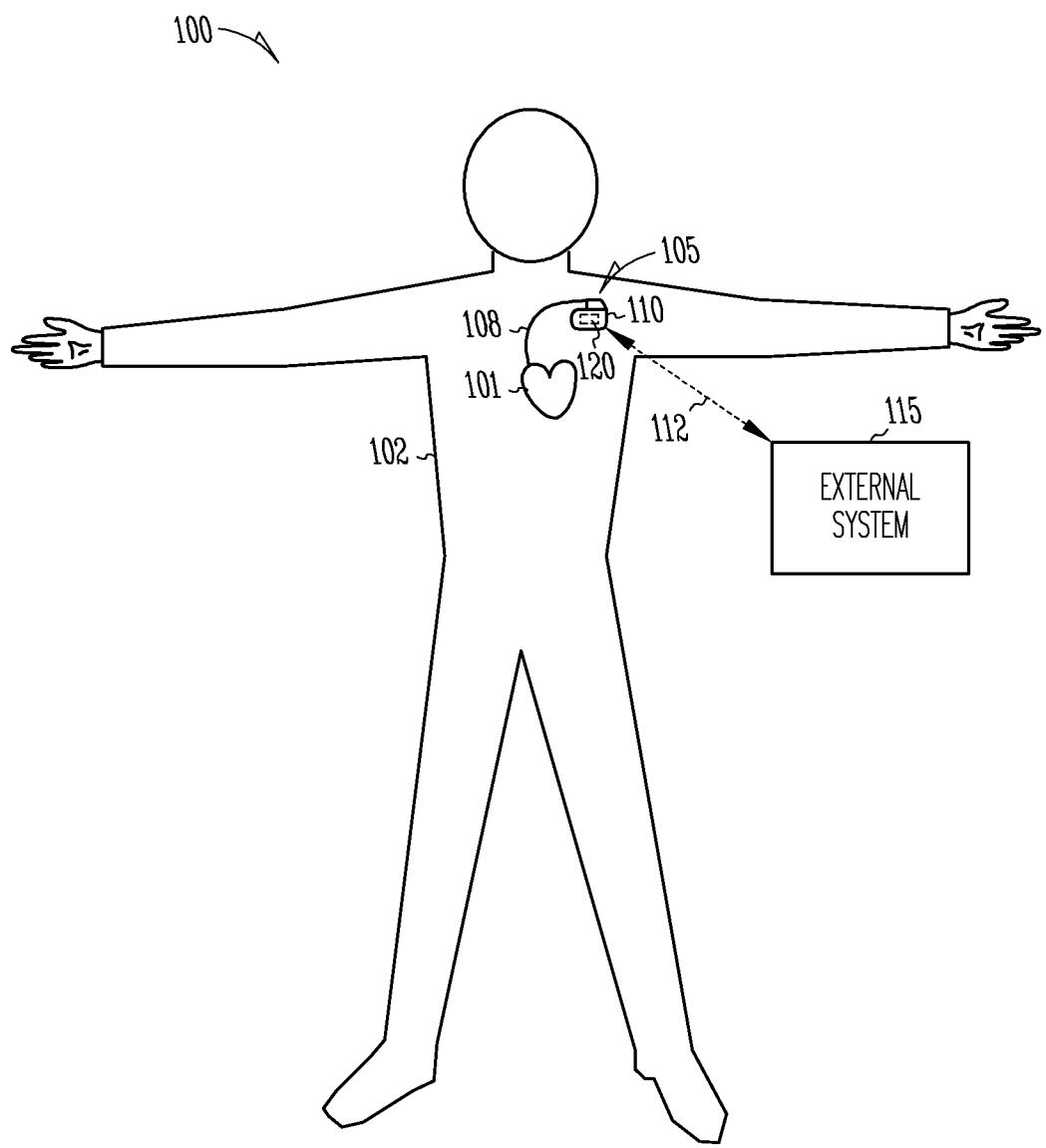
FIG. 1 is an illustration of an embodiment of a CRM system and portions of the environment in which the CRM system operates.

FIG. 1 is an illustration of an embodiment of a CRM system 100 and portions of an environment in which system 100 operates. System 100 includes an implantable system 105, an external system 115, and a telemetry link 112 providing for communication between implantable system 105 and external system 115.

Implantable system 105 includes implantable medical device 110 and lead system 108. In various embodiments, implantable medical device 110 is an implantable CRM device including one or more of a pacemaker, a cardioverter/defibrillator, a cardiac resynchronization therapy (CRT) device, a cardiac remodeling control therapy (RCT) device, a neruostimulator, a drug delivery device or a drug delivery controller, and a biological therapy device. As illustrated in FIG. 1, implantable medical device 110 is implanted in a patient's body 102. In various embodiments, lead system 108 includes leads for sensing physiological signals and delivering pacing pulses, cardioversion/defibrillation shocks, neurostimulation, pharmaceutical agents, biological agents, and/or other types of energy or substance for treating cardiac disorders. In various embodiments, electrodes placed in the patient's heart 101 or other portions of body 102 are used to sense physiological signals and deliver pacing pulses, cardioversion/defibrillation shocks, neurostimulation, pharmaceutical agents, biological agents, and/or other types of energy or substance for treating cardiac disorders. In one embodiment, lead system 108 includes one or more pacing-sensing leads each including at least one electrode placed in or on heart 101 for sensing one or more electrograms and/or delivering pacing pulses. In one embodiment, lead system 108 allows pacing pulses to be delivered to multiple atrial and ventricular sites.

Implantable medical device 110 includes a cardiac pacing system 120 that intermittently delivers stress augmentation pacing to heart 101 while ensuring patent safety and therapy efficiency by monitoring and responding to the patient's various conditions and activities. In various embodiments, in addition to the stress augmentation pacing, implantable medical device 110 also delivers one or more other cardiac pacing therapies, such as bradycardia pacing therapy, CRT, and RCT. In one embodiment, implantable medical device 110 controls the delivery of one or more of other therapies such as neurostimulation therapy, drug therapy, and biologic therapy in coordination with the stress augmentation pacing. Various embodiments of cardiac pacing system 120 are further discussed below in this document.

Implantable medical device 110 includes a hermetically sealed can to house electronic circuitry that performs sensing and therapeutic functions. In one embodiment, cardiac pacing system 120 is housed within the hermetically sealed can. In another embodiment, cardiac pacing system 120 includes internal components housed within the hermetically sealed can and external components located external to the hermetically sealed can but communicatively coupled to the internal components.

External system 115 allows a user such as a physician or other caregiver or the patient to control the operation of implantable medical device 110 and obtain information acquired by implantable medical device 110. In one embodiment, external system 115 includes a programmer communicating with implantable medical device 110 bi-directionally via telemetry link 112. In another embodiment, external system 115 is a patient management system including an external device communicating with a remote device through a telecommunication network. The external device is within the vicinity of implantable medical device 110 and communicates with implantable medical device 110 bi-directionally via telemetry link 112. The remote device allows the user to monitor and treat a patient from a distant location.

Telemetry link 112 provides for data transmission from implantable medical device 110 to external system 115. This includes, for example, transmitting real-time physiological data acquired by implantable medical device 110, extracting physiological data acquired by and stored in implantable medical device 110, extracting therapy history data stored in implantable medical device 110, and extracting data indicating an operational status of implantable medical device 110 (e.g., battery status and lead impedance). Telemetry link 112 also provides for data transmission from external system 115 to implantable medical device 110. This includes, for example, programming implantable medical device 110 to acquire physiological data, programming implantable medical device 110 to perform at least one self-diagnostic test (such as for a device operational status), and programming implantable medical device 110 to deliver one or more therapies.

Figure 2:
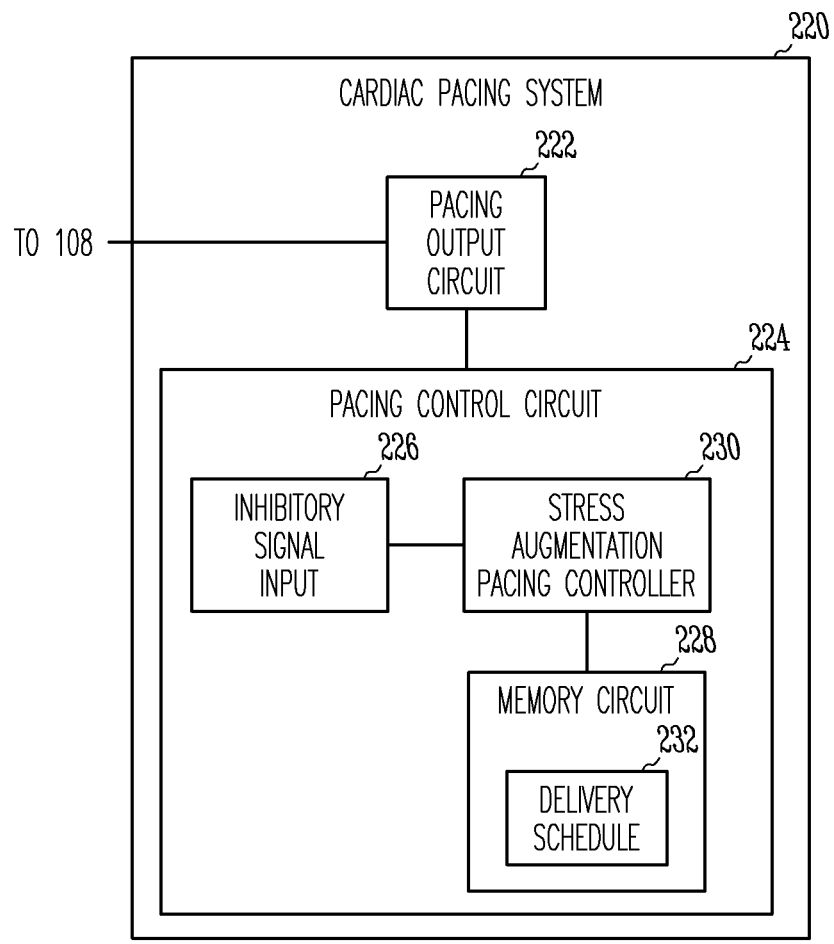
FIG. 2 is a block diagram illustrating an embodiment of a cardiac pacing system for delivering cardiac stress augmentation pacing.

FIG. 2 is a block diagram illustrating an embodiment of a cardiac pacing system 220 for delivering stress augmentation pacing. Cardiac pacing system 220 represents an embodiment of cardiac pacing system 120 and includes a pacing output circuit 222 and a pacing control circuit 224. Pacing output circuit 222 delivers pacing pulses to heart 101 through lead system 108. Pacing control circuit 224 controls the delivery of the pacing pulses and includes an inhibitory signal input 226, a stress augmentation pacing controller 230, and a memory circuit 228. Memory circuit 228 stores a delivery schedule 232 that is programmed into cardiac pacing system 220. Delivery schedule 232 specifies timing of stress augmentation pacing sessions each including a session duration during which the pacing pulses are delivered using pacing parameters selected to augment cardiac stress to a level effective for slowing or stopping progression of a cardiac disorder, such as heart failure. Inhibitory signal input 226 receives an inhibitory signal. Stress augmentation pacing controller 230 initiates each stress augmentation pacing session according to delivery schedule 232 if the inhibitory signal is not present at the scheduled beginning of that stress augmentation pacing session, and reschedules one or more stress augmentation pacing sessions if the inhibitory signal is present at the scheduled beginning of that stress augmentation pacing session.

In various embodiments, cardiac pacing system 220, including its various elements in various embodiments, is implemented using a combination of hardware and software. In various embodiments, each element of cardiac pacing system 220 may be implemented using an application-specific circuit constructed to perform one or more specific functions or a general-purpose circuit programmed to perform such function(s). Such a general-purpose circuit includes, but is not limited to, a microprocessor or a portion thereof, or other programmable logic circuit or a portion thereof. In one embodiment, pacing control circuit 224 is implemented as a microprocessor-based circuit programmed to perform various functions selected from those discussed in this document.

In one embodiment, the stress augmentation pacing sessions each include alternating non-pacing and pacing periods. The non-pacing periods each have a non-pacing duration during which no pacing pulse is timed to be delivered. The pacing periods each have a specified pacing duration during which a plurality of pacing pulses is timed to be delivered using pacing parameters selected to augment cardiac stress to a level effective for slowing or stopping progression of a cardiac disorder. In another embodiment, the stress augmentation pacing sessions each include alternating first and second pacing periods. The first pacing periods each have a first pacing duration during which a plurality of pacing pulses is timed to be delivered according to a first pacing mode. The second pacing periods each have a second pacing duration during which a plurality of pacing pulses is timed to be delivered according to a second pacing mode, using pacing parameters selected to augment cardiac stress to a level effective for slowing or stopping progression of a cardiac disorder. In various embodiments, delivery schedule 232 also specifies pacing parameters used in each of the stress augmentation pacing sessions.

Figure 3:
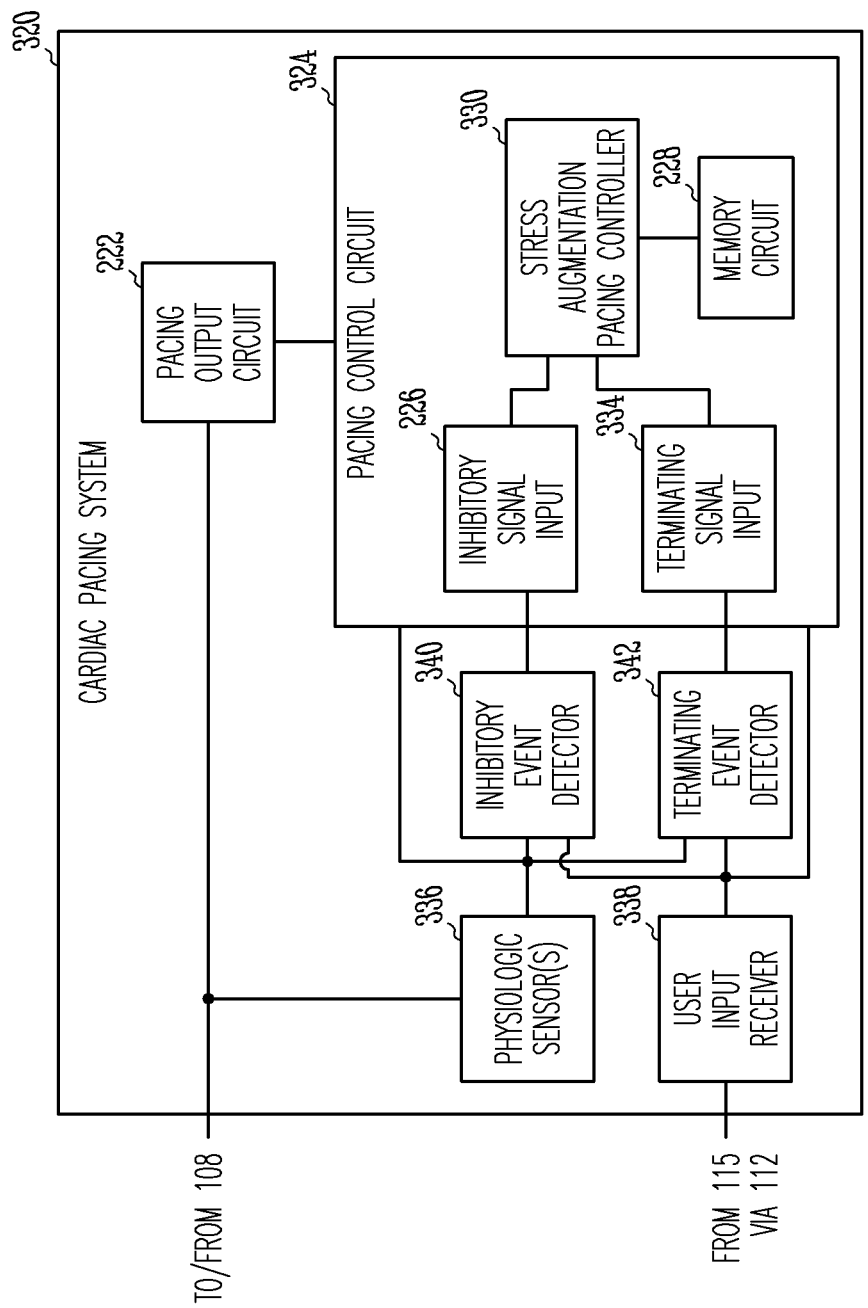
FIG. 3 is a block diagram illustrating another embodiment of the cardiac pacing system.

FIG. 3 is a block diagram illustrating an embodiment of a cardiac pacing system 320, which represents another embodiment of cardiac pacing system 120. Cardiac pacing system 320 includes pacing output circuit 222, a pacing control circuit 324, one or more physiological sensors 336, a user input receiver 338, an inhibitory event detector 340, and a terminating event detector 342, Pacing control circuit 324 represents an embodiment of pacing control circuit 224 and includes inhibitory signal input 226, a terminating signal input 334, memory circuit 228, and a stress augmentation pacing controller 330. Inhibitory signal input 226 receives the inhibitory signal. Terminating signal input 334 receives a terminating signal. Stress augmentation pacing controller 330 initiates each stress augmentation pacing session according to delivery schedule 232 when the inhibitory signal is not present at the scheduled beginning of that stress augmentation pacing session, and reschedules one or more of the stress augmentation pacing sessions when the inhibitory signal is present at the scheduled beginning of that stress augmentation pacing session. The rescheduling includes modification of the timing for initiating the subsequent one or more stress augmentation pacing sessions. In one embodiment, the rescheduling also includes adjustment of the pacing parameters used in the subsequent one or more stress augmentation pacing sessions, in addition to the modification of the timing for initiating the subsequent one or more stress augmentation pacing sessions. Stress augmentation pacing controller 330 times the delivery of the pacing pulses during each stress augmentation pacing session after the session is initiated. In response to the terminating signal received during a stress augmentation pacing session, stress augmentation pacing controller 330 terminates that session.

Inhibitory event detector 340 detects inhibitory events and produces the inhibitory signal in response to the detection of at least one of the inhibitory events. The inhibitory events are each associated with a physiologic condition, a pathologic condition, or a medical treatment considered as potentially reducing effectiveness of the stress augmentation pacing. In various embodiments, inhibitory event detector 340 detects each of the inhibitory events from a physiological signal or a user signal. The physiological signal is sensed by a sensor of physiological sensor(s) 336. The user signal is received by user input receiver 338 from a user such as the patient.

Terminating event detector 342 detects terminating events and produces the terminating signal in response to the detection of at least one of the terminating events. The terminating events are each associated with a physiologic condition, a pathologic condition, or a medical treatment considered to potentially compromise safety of stress augmentation pacing. In various embodiments, terminating event detector 342 detects each of the terminating events from a physiological signal or a user signal. The physiological signal is sensed by a sensor of physiological sensor(s) 336. The user signal is received by user input receiver 338 from a user such as the patient. In one embodiment, one or more types of the terminating events are also used as the inhibitory events.

In various embodiments, one or more sensors of physiological sensor(s) 336 are incorporated into or onto implantable medical device 110, incorporated into one or more implantable leads of lead system 108, and/or communicatively coupled to implantable medical device 110 via conductors or telemetry. Examples of physiological sensor(s) 336 are discussed below with reference to FIG. 4.

User input receiver 338 receives the user signals. In one embodiment, external system 115 includes a user input device to receive the user signals. In various embodiments, the user signals indicate the patient's intake of drug and/or food. The stress augmentation pacing may be ineffective or harmful to the patient for a period of time following administration of certain drugs such as Beta-blocker, satins, and insulin. The stress augmentation pacing may also be ineffective or harmful to the patient with a high blood glucose level, such as during a period of time following a meal. Thus, examples of the user signals include a drug signal indicative of an administration of a specified type drug and a food signal indicative of substantial food consumption. In one embodiment, inhibitory event detector 340 produces the inhibitory signal in response to the receipt of the user signal. In one embodiment, the inhibitory signal is present for a programmed period of time following the receipt of the user signal. In one embodiment, terminating event detector 342 produces the terminating signal in response to the receipt of the user signal.

Figure 4:
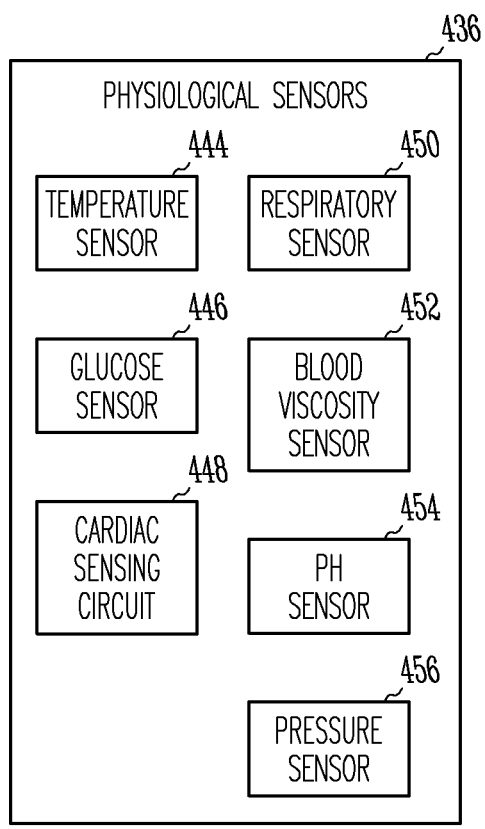
FIG. 4 is a block diagram illustrating an embodiment of physiological sensors of the cardiac pacing system.

FIG. 4 is a block diagram illustrating an embodiment of physiological sensors 436. Physiological sensors 436 represent an embodiment of physiological sensor(s) 336. In the illustrated embodiment, physiological sensors 436 include, by way of example, a temperature sensor 444, a glucose sensor 446, a cardiac sensing circuit 448, a respiratory sensor 450, a blood viscosity sensor 452, a pH sensor 454, and a pressure sensor 456. In various embodiments, physiological sensors 436 includes any one or more of temperature sensor 444, glucose sensor 446, cardiac sensing circuit 448, respiratory sensor 450, blood viscosity sensor 452, pH sensor 454, pressure sensor 456, and other sensors capable of sensing signals indicative of the inhibitory and/or terminating events.

Temperature sensor 444 senses body temperature of the patient. The stress augmentation pacing is likely ineffective when the patient's body temperature is high, such as during fever, inflammation, or exercise. In various embodiments, temperature sensor 444 is incorporated into implantable medical device 110 or lead system 108 Inhibitory event detector 340 produces the inhibitory signal when the body temperature exceeds a specified threshold temperature. In one embodiment, the inhibitory signal is present while the temperature is above the specified threshold temperature.

Glucose sensor 446 senses a glucose signal indicative of a blood glucose level of the patient. The stress augmentation pacing therapy may be ineffective when the patient's blood glucose level is high, such as when the patient has diabetes. Inhibitory event detector 340 produces the inhibitory signal when the blood glucose level exceeds a specified threshold level. In one embodiment, the inhibitory signal is present while the blood glucose level is above the specified threshold level.

Cardiac sensing circuit 448 senses one or more cardiac signals for controlling delivery of the pacing pulses and for cardiac ischemia detection. If acute cardiac ischemia develops during a stress augmentation pacing session, the session is to be terminated. ST elevation is used as an indication of ischemia. Terminating event detector 342 produces the terminating signal in response to the amplitude of an ST segment of at least one cardiac signal of the one or more cardiac signals exceeding a specified threshold amplitude.

Respiratory sensor 450 senses one or more respiratory signals indicative of one or more respiratory parameters. A change in the patient's breathing pattern may indicate that the patient's heart is overly stressed to a potentially harmful level by the stress augmentation pacing. In one embodiment, respiratory sensor 450 includes an impedance sensor. In one embodiment, respiratory sensor 450 includes a minute ventilation sensor that is also used for pacing rate control under a rate-adaptive pacing mode. Terminating event detector 342 produces the terminating signal in response to a substantial change in the respiratory pattern as indicated by a substantial change in one or more values of the one or more respiratory parameters.

Blood viscosity sensor 452 senses a signal indicative of a blood viscosity. A high blood viscosity indicates that the patient is dehydrated and should not receive the stress augmentation pacing Inhibitory event detector 340 produces the inhibitory signal when the blood viscosity exceeds a specified threshold level. In one embodiment, the inhibitory signal is present while the blood viscosity is above the specified threshold level.

PH sensor 454 senses a blood pH value. A high blood acidity (i.e., low pH) level indicates that the patient is overly stressed and should not receive the stress augmentation pacing. Inhibitory event detector 340 produces the inhibitory signal when the blood pH value is below a specified threshold value. In one embodiment, the inhibitory signal is present while the blood pH value is below the specified threshold level.

Pressure sensor 456 senses a blood pressure and/or changes in the blood pressure. Systolic and diastolic arterial pressures naturally vary between heart beats and vary in a circadian rhythm. They change in response to stress, nutritional factors, drugs, disease, exercise, and momentarily from standing up. Acute bouts of hypertension (abnormally high blood pressure) indicates that mechanical stress on the heart may be abnormally high, and that the heart may not respond to the stress augmentation pacing or may respond negatively to the stress augmentation pacing. Hypotension (abnormally low blood pressure) indicates that cardiac output may be low, and thus the stress augmentation pacing may be dangerous for further decreasing the cardiac output. Inhibitory event detector 340 produces the inhibitory signal when the change in blood pressure exceeds a specified threshold value, and/or when the blood pressure is below a specified value.

While each sensor illustrated on FIG. 4 is discussed in association with one of the inhibitory signal and the terminating signal, signals sensed by these sensors may be used for producing any or both of the inhibitory and terminating signals, depending on the patient's specific needs and conditions. In various embodiments, one or both of the terminating events and inhibitory events are detected from each of the body temperature, the glucose signal, the one or more cardiac signals, the one or more respiratory signals, the signal indicative of blood viscosity, the blood pH value, the blood pressure, and the change in blood pressure. In one embodiment, the selection of sensor(s) and the use of each sensed signal for producing the inhibitory and/or terminating signals are programmable by a physician or other caregiver using external system 115.

Figure 5:
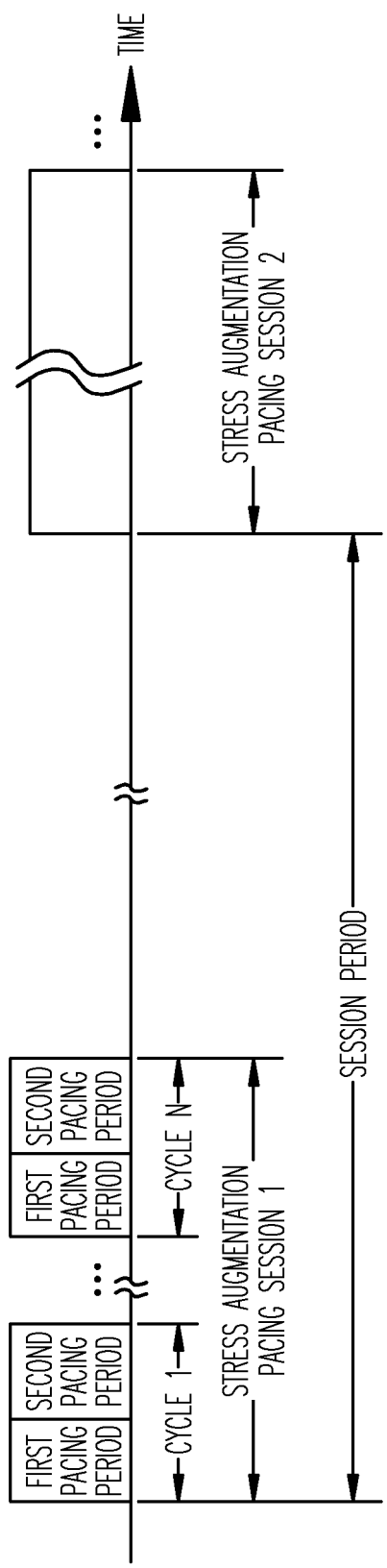
FIG. 5 is a timing diagram illustrating an embodiment of timing of a delivery schedule specifying cardiac stress augmentation pacing sessions.

FIG. 5 is a timing diagram illustrating an embodiment of timing of a delivery schedule specifying stress augmentation pacing sessions, as an example of delivery schedule 232. The stress augmentation pacing, also known as intermittent pacing and cardioprotective pacing, protects the heart from cardiac disorders such as ischemia, infarction, and heart failure by creating or augmenting regional stress in the heart for brief periods of time to activate and/or enhance the patient's intrinsic cardiac protective mechanisms. In the illustrated embodiment, the delivery schedule specifies stress augmentation pacing sessions delivered on a periodic basis at a session frequency (or period as marked in FIG. 5). Each stress augmentation pacing session includes N cycles of alternating first and second pacing periods. Each cycle includes a first pacing period followed by a second pacing period. The first pacing period has a first pacing duration during which the delivery of the pacing pulses is controlled according to a first pacing mode. The second pacing period has a second pacing duration during which the delivery of the pacing pulses is controlled according to the second pacing mode.

In one embodiment, the first pacing period is a non-pacing period having a first pacing duration during which no pacing pulse is timed to be delivered according to a non-pacing mode, and the second pacing period is a stress augmentation pacing period having a second pacing duration during which pacing pulses are timed to be delivered according to a stress augmentation pacing mode. When a pacing pulse is timed to be delivered, it will be delivered unless being inhibited by a detected intrinsic cardiac depolarization occurring before the scheduled delivery of the pacing pulse during a cardiac cycle. Under the non-pacing mode according to which no pacing pulse is timed to be delivered, the non-delivery is due to programming rather than inhibition by a detected intrinsic cardiac depolarization. Under the stress augmentation pacing mode, pacing pulses are delivered to augment mechanical stress on the myocardium to a level effecting cardioprotection against myocardial injury or deterioration. In various embodiments, the stress augmentation pacing mode is a standard or non-standard pacing mode with pacing parameter values selected for the desired level of myocardial stress augmentation according to the patients' needs, conditions, and responses. In one embodiment, the stress augmentation pacing mode is an atrial tracking pacing mode with an atrio-ventricular (AV) pacing delay that is substantially shorter than the patient's intrinsic AV conduction interval. In another embodiment, the stress augmentation pacing mode is a bradycardia pacing mode with a pacing rate substantially higher than the patient's intrinsic heart rate. In another embodiment, the stress augmentation pacing mode is an asynchronous pacing mode with a pacing rate substantially higher than the patient's intrinsic heart rate.

In another embodiment, the first pacing period is a back-up pacing period having a first pacing duration during which pacing pulses are timed to be delivered according to a back-up pacing mode, and the second pacing period is a stress augmentation pacing period having a second pacing duration during which the delivery of the pacing pulse is controlled according to the stress augmentation pacing mode. In one embodiment, the backup pacing mode is a chronic pacing mode that is substantially different from the stress augmentation pacing mode and applied before and/or after the stress augmentation pacing session. In one embodiment, the back-up pacing mode is an anti-bradycardia pacing mode according to which pacing pulses are timed to be delivered as an anti-bradycardia therapy. In another embodiment, the back-up pacing mode is a cardiac resynchronization mode according to which pacing pulses are timed to be delivered as a cardiac resynchronization therapy (CRT). In another embodiment, the back-up pacing mode is a cardiac remodeling control mode according to which pacing pulses are timed to be delivered as a cardiac remodeling control therapy (RCT).

In various embodiments, the session frequency (or period), the number of the cycles (N), the first pacing period, and the second pacing period are each programmable. In one embodiment, the session frequency is programmable between approximately 1 and 12 sessions each day. The number of cycles (N) for each stress augmentation pacing session is programmable between approximately 3 and 12 cycles. The first and second pacing periods are each programmable between approximately 5 and 16 minutes. In one embodiment, the first pacing duration is substantially equal to the second pacing duration. In various embodiments, the values of these parameters are determined based on the patient's physiological and pathological conditions, tolerance to the stress augmentation pacing therapy, and responsiveness to the stress augmentation pacing therapy known to associate with certain values or value ranges of the parameters. For example, the patient may need a relatively large number of stress augmentation pacing sessions each with a relatively low intensity (i.e., relatively low level of elevation or duration of cardiac stress augmentation), or a relatively small number of stress augmentation pacing sessions each with a relatively high intensity.

Figure 6:
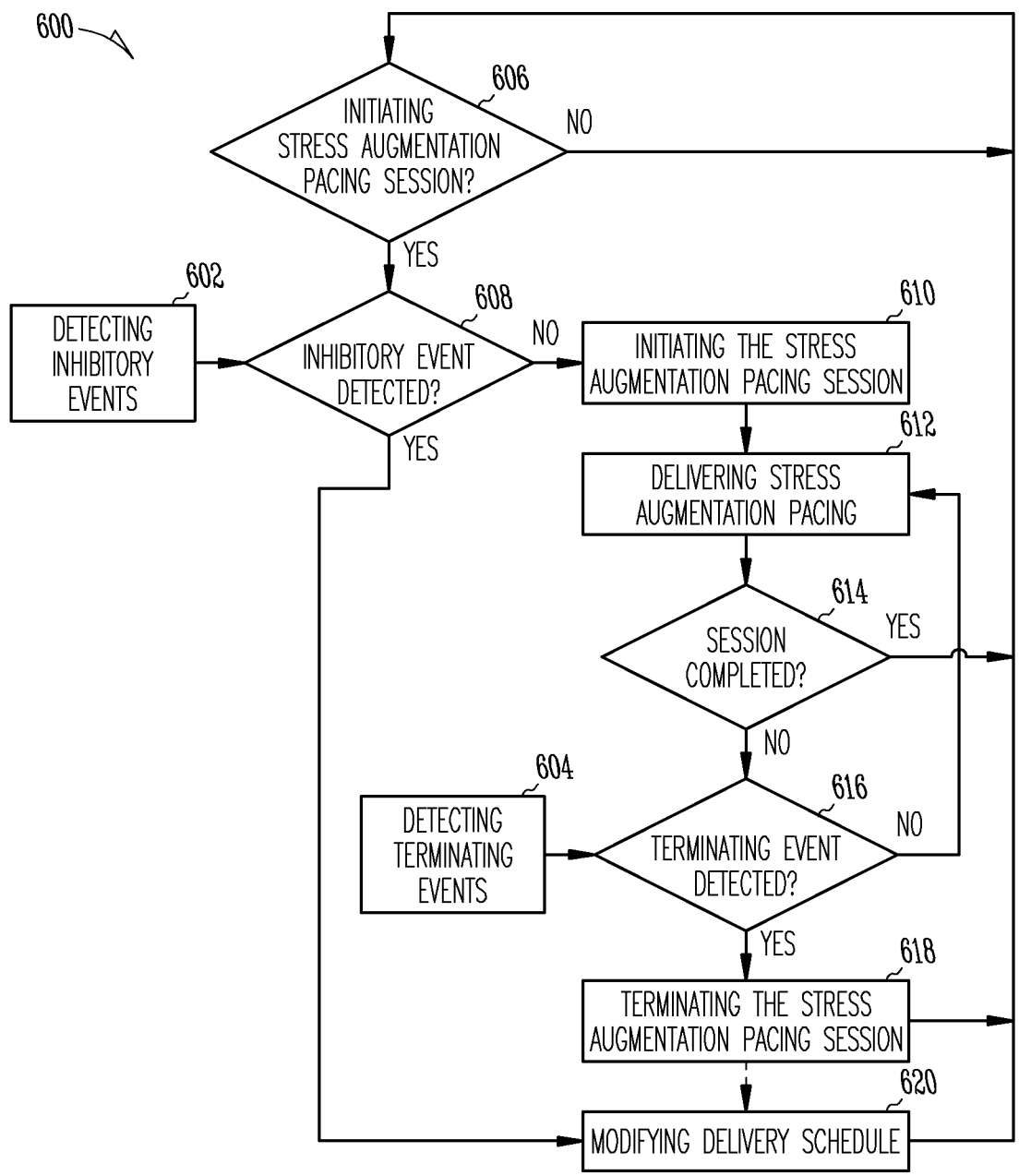
FIG. 6 is a flow chart illustrating a method for cardiac stress augmentation pacing.

FIG. 6 is a flow chart illustrating a method 600 for stress augmentation pacing. In one embodiment, the method is performed by system 100, including various embodiments of its elements as discussed in this document. Method 600 is used to control delivery of stress augmentation pacing sessions as specified in a delivery schedule, with safety and efficiency of the pacing ensured by detecting and responding to various inhibitory and terminating events. The inhibitory events are each associated with a physiologic condition, a pathologic condition, or a medical treatment and considered as potentially reducing effectiveness of stress augmentation pacing. The terminating events are each associated with a physiologic condition, a pathologic condition, or a medical treatment and considered as potentially increasing risk of stress augmentation pacing.

At 602, the inhibitory events are detected. In various embodiments, the inhibitory events are each detected from a physiological signal sensed by a physiological sensor or a user signal received from a user such as a physician or other caregiver or the patient receiving the stress augmentation pacing. Examples of the inhibitory events include high body temperature, high blood glucose level, high blood viscosity, high blood acidity, recent dose of specified drugs, and recent food consumption, as discussed above with reference to FIG. 5.

At 604, the terminating events are detected. In various embodiments, the terminating events are also each detected from a physiological signal sensed by a physiological sensor or a user signal received from a user such as a physician or other caregiver or the patient receiving the stress augmentation pacing. Examples of the terminating events include acute cardiac ischemia, excessive cardiac stress, recent dose of specified drugs, and recent food consumption, as discussed above with reference to FIG. 5. In one embodiment, some types of events are used as both inhibitory and terminating events.

At 610, if a stress augmentation pacing session is to be initiated at 606 according to the delivery schedule, and no inhibitory event is detected at 608, the stress augmentation pacing session is initiated. At 612, the stress augmentation pacing is delivered. If a stress augmentation pacing session is to be initiated according to the delivery schedule at 606, but an inhibitory event is detected at 608, the delivery schedule is modified by rescheduling one or more stress augmentation pacing sessions at 620. In one embodiment, the delivery schedule is further modified by adjusting pacing parameters for the one or more stress augmentation pacing sessions.

At 618, if the stress augmentation pacing session has not been completed at 614, but a terminating event is detected at 616, the stress augmentation pacing session is terminated. If the stress augmentation pacing session has not been completed at 614, and no terminating event is detected at 616, the delivery at 612 continues until the session is completed at 614. After the session is completed at 614 without being terminated by the terminating event, the next session is to be initiated according to the delivery schedule. In one embodiment, if a session is prematurely terminated by the terminating event at 618, the next session is still to be initiated according to the delivery schedule. In another embodiment, if a session is prematurely terminated by the terminating event at 618, the delivery schedule is modified by rescheduling one or more stress augmentation pacing sessions at 620, when the detection of the terminating event indicates or suggests that the patient may benefit from the modification. In one embodiment, the delivery schedule is further modified by adjusting pacing parameters for the one or more stress augmentation pacing sessions.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A cardiac pacing system, comprising:
    a pacing output circuit adapted to deliver pacing pulses; and
    a pacing control circuit coupled to the pacing output circuit and adapted to control the delivery of the pacing pulses, the pacing control circuit including:
        a memory circuit storing a delivery schedule specifying timing for initiating stress augmentation pacing sessions each including a session duration during which the pacing pulses are delivered using pacing parameters selected to augment myocardial mechanical stress to a level effecting cardioprotection against myocardial injury or deterioration by increasing a degree of ventricular asynchrony; wherein the delivery schedule is programmed to specify the stress augmentation pacing sessions to be delivered on a periodic basis at a session frequency between approximately 1 and 12 sessions each day and each including alternating non-pacing and pacing periods, the non-pacing periods each having a non-pacing duration during which no pacing pulse is timed to be delivered, the pacing periods each having a specified pacing duration during which a plurality of the pacing pulses is timed to be delivered using pacing parameters selected to augment myocardial mechanical stress to the level effecting cardioprotection against myocardial injury or deterioration; an inhibitory signal input to receive an inhibitory signal indicative of detection of an event potentially reducing effectiveness of stress augmentation pacing during each of the stress augmentation pacing sessions; and
        a stress augmentation pacing controller coupled to the memory circuit and the inhibitory signal input, the stress augmentation pacing controller programmed to initiate each of the stress augmentation pacing sessions according to the delivery schedule if the inhibitory signal is not present at a scheduled beginning of the each of the stress augmentation pacing sessions and modify the delivery schedule by rescheduling one or more of the stress augmentation pacing sessions if the inhibitory signal is present at the scheduled beginning of the each of the stress augmentation pacing sessions.

2. The system of claim 1, comprising:
    one or more physiological sensors adapted to sense one or more physiological signals; and
    an inhibitory event detector adapted to detect inhibitory events from at least a first physiological signal of the sensed one or more physiological signals and produce the inhibitory signal in response to a detection of at least one of the inhibitory events.

3. The system of claim 2, comprising a user input receiver adapted to receive one or more user signals, and wherein the inhibitory event detector is adapted to detect inhibitory events from at least the first physiological signal and a first user signal of the user signals.

4. The system of claim 3, wherein the pacing control circuit comprises a terminating signal input to receive a terminating signal, and the stress augmentation pacing controller is programmed to terminate each of the cardiac stress augmentation pacing sessions in response to the terminating signal received during the each of the stress augmentation pacing sessions.

5. The system of claim 4, comprising a terminating event detector adapted to detect terminating events using at least one of a second physiological signal of the sensed one or more physiological signals and a second user signal of the user signals and adapted to produce the terminating signal in response to a detection of at least one of the terminating events.

6. The system of claim 5, wherein the one or more physiological sensors comprise a temperature sensor adapted to sense a body temperature, and the inhibitory event detector is adapted to produce the inhibitory signal when the sensed body temperature exceeds a specified threshold temperature.

7. The system of claim 5, wherein the one or more physiological sensors comprise a glucose sensor adapted to sense a glucose signal indicative of a blood glucose level, and the inhibitory event detector is adapted to produce the inhibitory signal when the blood glucose level exceeds a specified threshold level.

8. The system of claim 5, wherein the one or more physiological sensors comprise a cardiac sensing circuit adapted to sense one or more cardiac signals, and the terminating event detector is adapted to produce the terminating signal in response to an amplitude of an ST segment of at least one cardiac signal of the one or more cardiac signals exceeding a specified threshold amplitude.

9. The system of claim 5, wherein the one or more physiological sensors comprise a respiratory sensor adapted to sense one or more respiratory signals indicative of one or more respiratory parameter, and the terminating event detector is adapted to produce the terminating signal in response to a substantial change in the respiratory pattern as indicated by a substantial change in one or more values of the one or more respiratory parameters.

10. The system of claim 5, wherein the user input receiver is adapted to receive a drug signal indicative of an administration of a specified drug, the inhibitory event detector is adapted to produce the inhibitory signal in response to receipt of the drug signal, and the terminating event detector is adapted to produce the terminating signal in response to the drug signal.

11. The system of claim 5, wherein the user input receiver is adapted to receive a food signal indicative of a substantial food consumption, the inhibitory event detector is adapted to produce the inhibitory signal in response to the food signal, and the terminating event detector is adapted to produce the terminating signal in response to receipt of the food signal.

12. A method for operating a cardiac pacing system, comprising:
    determining whether an inhibitory signal is present before initiating each of stress augmentation pacing sessions according to a delivery schedule using an implantable medical device, the inhibitory signal indicative of detection of an event potentially reducing effectiveness of stress augmentation pacing during the each of stress augmentation pacing sessions, the stress augmentation pacing sessions each including a session duration during which pacing pulses are delivered from the implantable medical device using pacing parameters selected to augment myocardial mechanical stress to a level effecting cardioprotection against myocardial injury or deterioration by increasing a degree of ventricular asynchrony, the delivery schedule stored in the implantable medical device and specifying timing for initiating the stress augmentation pacing sessions; timing the stress augmentation pacing sessions to be delivered on a periodic basis at a session frequency between approximately 1 and 12 sessions each day; and timing the delivery of the pacing pulses during the each of the stress augmentation pacing sessions, including timing alternating non-pacing and pacing periods, the non-pacing periods each having a non-pacing duration during which no pacing pulse is timed to be delivered, the pacing periods each having a specified pacing duration during which a plurality of the pacing pulses is timed to be delivered using pacing parameters selected to augment rnyocardial mechanical stress to the level effecting cardioprotection against myocardial injury or deterioration; initiating the each of the stress augmentation pacing sessions according to the delivery schedule using the implantable medical device if the inhibitory signal is not present; and modifying the delivery schedule by rescheduling one or more of the stress augmentation pacing sessions using the implantable medical device if the inhibitory signal is present.

13. The method of claim 12, comprising:

sensing one or more physiological signals;

detecting inhibitory events using at least a first physiological signal of the sensed one or more physiological signals; and producing the inhibitory signal m response to a detection of at least one of the inhibitory events.

14. The method of claim 13, comprising:

receiving user signals from a user; and detecting the inhibitory events using at least the first physiological signal and a first user signal of the user signals.

15. The method of claim 14, comprising:

detecting terminating events using at least one of a second physiological signal of the sensed one or more physiological signals and a second user signal of the user signals; and terminating the each of the cardiac stress augmentation pacing sessions in response to a detection of at least one of the terminating events during the each of the stress augmentation pacing sessions.

16. The method of claim 15, wherein sensing the one or more physiological signals comprises sensing a body temperature, and producing the inhibitory signal comprises producing the inhibitory signal when the body temperature exceeds a specified threshold temperature.

17. The method of claim 15, wherein sensing the one or more physiological signals comprises sensing a glucose signal indicative of a blood glucose level, and producing the inhibitor signal comprises producing the inhibitory signal when the blood glucose level exceeds a specified threshold level.

18. The method of claim 15, wherein sensing the one or more physiological signals comprises sensing one or more cardiac signals, and producing the terminating signal comprises producing the terminating signal in response to an amplitude of an ST segment of at least one cardiac signal of the one or more cardiac signals exceeding a specified threshold amplitude.

19. The method of claim 15, wherein sensing the one or more physiological signals comprises sensing one or more respiratory signals indicative of one or more respiratory parameter, and producing the terminating signal comprises producing the terminating signal in response to a substantial change in the respiratory pattern as indicated by a substantial change in one or more values of the one or more respiratory parameters.

20. The method of claim 15, wherein receiving the user signals comprises receiving a drug signal indicative of an administration of a specified drug, producing the inhibitory signal comprises producing the inhibitory signal in response to receipt of the drug signal, and producing the terminating signal comprises producing the terminating signal in response to receipt of the drug signal.

21. The method of claim 15, wherein receiving the user signals comprises receiving a food signal indicative of a substantial food consumption, producing the inhibitory signal comprises producing the inhibitory signal in response to receipt of the drug signal, and producing the terminating signal comprises producing the terminating signal in response to receipt of the food signal.

* * * * *